United States Patent [19]

Gilbert

[11] 4,221,746

[45] Sep. 9, 1980

[54] PREPARATION OF HEXANITROSTILBENE

[75] Inventor: Everett E. Gilbert, Morristown, N.J.

[73] Assignee: The United States of America as represented by the Secretary of the Army, Washington, D.C.

[21] Appl. No.: 20,889

[22] Filed: Mar. 15, 1979

[51] Int. Cl.³ .............................................. C07C 79/10
[52] U.S. Cl. .................................................... 568/931
[58] Field of Search ................. 149/105; 260/645, 646

[56] References Cited

U.S. PATENT DOCUMENTS

| 3,699,176 | 10/1972 | Syrop | 260/645 |
|---|---|---|---|
| 4,085,152 | 4/1978 | Salter et al. | 260/645 |

*Primary Examiner*—Leland A. Sebastian
*Attorney, Agent, or Firm*—Nathan Edelberg; Robert P. Gibson; A. Victor Erkkila

[57] ABSTRACT

There is disclosed a process for converting 2,2', 4,4', 6,6'-hexanitrobibenzyl (HNBB) to 2,2', 4,4', 6,6'-hexanitrostilbene (HNS) in high yields by reacting HNBB with a halogenating agent in the presence of a base in an organic solvent or a liquid suspending agent. A preferred halogenating agent is bromine; a preferred base is pyridine; a preferred solvent is dimethylformamide; and a preferred liquid suspending agent is toluene or chlorobenzene.

16 Claims, No Drawings

PREPARATION OF HEXANITROSTILBENE

GOVERNMENT RIGHTS

The invention described herein may be manufactured, used and licensed by the Government for Governmental purposes without the payment to me of any royalties thereon.

BACKGROUND OF THE INVENTION 2,2',4,4',6,6'-hexanitrostilbene (HNS) is a thermally-stable explosive. It is also especially useful as a crystal modifying additive in melt-cast 2,4,6 trinitrotoluene (TNT) as disclosed in U.S. Pat. No. 3,620,857.

HNS has been prepared by oxidation of TNT. However, the process has not been entirely satisfactory, since the yields based on the starting material TNT have been uneconomically low.

Thus, HNS can be prepared according to the process disclosed in U.S. Pat. No. 3,505,413 by the action of sodium hypochlorite on TNT at 15° C. in tetrahydrofuran/methanol solution. The yield of HNS obtained by this method is typically about 30–35% after acetone washing to remove the bulk of coprecipitated impurities, chiefly dipicryl ethane, also known as hexanitrobibenzyl (HNBB). In addition the crude HNS produced in about 40–45% yeild contains large amounts of an impurity, the so-called "red oil," believed to consist chiefly of trinitrobenzyl chloride, trinitrobenzaldehyde, trinitrobenzylalcohol, trinitrobenzoic acid, and trinitrobenzene, which causes difficulty in separating the HNS product and reuse of the tetrahydrofuran solvent.

This process is also described in Shipp et al, J. Org. Chem. 31, 857 (1966).

In an effort to improve yields, Salter et al, British Patent Application 76/2501, Jan. 22, 1976, U.S. Pat. No. 4,085,152, treated TNT in tetrahydrofuran/methanol with aqueous sodium hypochlorite at a temperature of about 10°–20° C., then added an aqueous solution of an organic amine, preferably trimethylamine. The yields of HNS produced by this process are about 50%.

Kompolthy et al, Hungarian Patent T/9639 VE-719 (CO6 f 9/04) developed a new procedure based on the air oxidation of TNT. They also observed that the preparation of HNS from TNT could be done in two steps as follows:

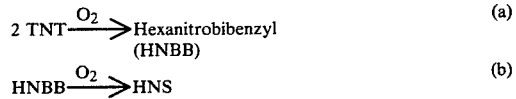

Shipp and Kaplan, Heat Resistant Explosives XVI, NOLTR 64–63, (1964) shows that TNT could be converted to HNBB or HNS using sodium hypochlorite under varied conditions, but they did not demonstrate any procedure for converting HNBB to HNS. Shipp and Kaplan obtained a 79% yield of HNBB from TNT.

Kompolthy et al obtained an 82% yield of HNBB and reported yields of 76–91% of HNS from HNBB using dimethylformamide or dimethylsulfoxide as solvents in a reaction mixture containing methanol, potassium hydroxide, copper sulfate and pyridine. This Kompolthy et al work has been repeated by others but yields of only 25–40% of HNS have been obtained.

There is therefore a need for a process for the production of HNS in high reproducible yields.

BRIEF SUMMARY OF THE INVENTION

This invention relates to the production of 2,2',4,4',6,6'-hexanitrostilbene (HNS) in high yields from 2,4,6 trinitrotoluene (TNT) via the intermediate 2,2',4,4',6,6'hexanitrobibenzyl (HNBB). More particularly, this invention involves the conversion of HNBB to HNS by reacting HNBB with a halogenating agent in the presence of an organic or inorganic base. The reaction is conducted in a suitable solvent or a liquid suspending agent.

DETAILED DESCRIPTION OF THE INVENTION

The present invention is based on the discovery that HNBB can be converted to HNS, often in good yields, if HNBB is reacted with a halogenating agent in the presence of a base and a suitable solvent or liquid suspending agent. The halogenating agents which are suitable for use in the process of this invention are those halogenating agents which are known to the art. Those which have been found to be suitable are chlorine, bromine, iodine, N-halogen derivatives, e.g. N-chlorosuccinimide, N-bromosuccinimide, and N-bromoacetamide, a hypohalites, e.g. sodium, potassium, or calcium hypochlorite, or hypobromite.

Halogenating agents preferred for use in this invention are bromine, chlorine, N-bromosuccinimide, N-bromacetamide, and N-chlorosuccinimide.

The bases which are suitable for use in this invention are any organic or inorganic base. Suitable inorganic bases include sodium hydroxide, ammonium hydroxide, magnesium oxide and sodium carbonate and bicarbonate. Suitable organic bases include tertiary amines such as pyridine and triethylamine. The base which is preferred for use in this invention is pyridine.

Liquid solvents or suspending agents which are suitable for use in this invention are those in which the reactants are readily dissolved or suspended and which do not interfere with the reaction. The following have been found to be suitable, water, dimethyl formamide, acetonitrile, tetrahydrofuran, 1,4-dioxane, pyridine, hexamethylphosphoramide, toluene, and chlorobenzene. Preferred for use in this invention are the liquid suspending agents, toluene and chlorobenzene. They are preferred because they can be easily recovered by decantation and reused, thereby virtually eliminating the cost of solvent recovery and recycle.

The reaction times and temperatures are not critical so long as the reactions are allowed by continue until completed. Generally the present process can be successfully run at from about one to four hours at temperatures from about 20° C. to about 100° C., although not limited thereto.

It is believed that the reaction of the present process involves the removal of two hydrogen atoms from the ethylene linkage of HNBB according to the following equation:

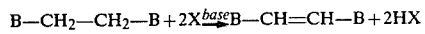

wherein X represents halogen and B represents 2,4,6-trinitrophenyl.

The amount of halogenating agent required theoretically according to the foregoing equation is at least two equivalents of halogenating agent (2atoms of halogen)

per mole of HNBB. The use of halogenating agent greatly in excess of this ratio can also be employed with good results. Thus, as shown in Example III, a high yield of HNS was obtained when the ratio employed was somewhat more than 3 mols (6 atoms) of bromine per mole of HNBB.

The base is essential for carrying out the reaction of the present invention, since relatively little or no HNS is obtained when the reaction is attempted in the absence of a base. (See Examples X, XI, XII, XIV, XVII and XX.) It is believed that the base functions to remove one or both protons from the ethylene linkage and neutralize the hydrogen halide formed in the reaction. The base can be utilized in an amount greatly exceeding that required to neutralize the hydrogen halide formed in the reaction. Liquid organic bases, such as pyridine, can function both as a base and as the liquid reaction medium, as shown in Example I.

The following examples illustrate the invention.

EXAMPLE I 1.2 g. HNBB, 1.0 g. bromine, and 25 ml. pyridine were mixed and stirred for three hours at room temperature. The reaction mixture was mixed with water, and the solid product which resulted was filtered and dried to yield 1.3 g. For purification the product was stirred for thirty minutes with 50 ml. acetone, filtered, and dried. The purified product thus obtained weighed 1 g., which corresponds to 83% of theory yield based on the HNBB employed. The HNS was identified by its infrared spectrum.

EXAMPLE II 1.2 g. HNBB, 0.6 g. of bromine, 0.6 g. pyridine, and 25 ml. dimethylformamide were mixed and heated for two hours at 100° C. The product which resulted was isolated from the reaction mixture and purified by extraction with acetone as in Example I, yielding 79% of HNS.

EXAMPLE III 1.2 g. HNBB, 1.2 g. bromine, 1.2 g. pyridine, and 25 ml. dimethylformamide were mixed and heated four hours at 70° C. The resulting product was recovered and purified as in Example I to give a yield of 92% of HNS.

EXAMPLE IV 1.2 g. HNBB, 1.2 g. bromine, 1.2 g. pyridine, and 25 ml. acetonitrile were mixed and heated four hours at 70° C. The product was recovered and purified as in Example I. The yield of HNS was 92%.

EXAMPLE V 1.2 g. HNBB, 1.2 g. bromine, 1.2 g. pyridine, and 25 ml. tetrahydrofuran were mixed and heated four hours at 70° C. The product was recovered and purified as in Example I. The yield of HNS was 83%.

EXAMPLE VI 1.2 g. of HNBB, 1.2 g. bromine, 1.2 g. pyridine, and 25 ml. 1,4-dioxane were mixed and heated four hours at 70° C. The product was recovered and purified as in Example I. A 67% yield of HNS was thus obtained.

EXAMPLE VII 1.2 g. HNBB, 1.2 g. bromine, 1.2 g. pyridine, and 50 ml. toluene (this was a suspending medium rather than a solvent) were mixed and heated four hours at 100° C. The reaction mixture was cooled and the toluene was separated by decantation. The solid product remaining was purified by extraction with acetone as described in Example I. The yield of HNS was 71%.

EXAMPLE VIII 1.2 g. HNBB, 1.2 g. bromine, 1.2 g. pyridine, and 50 ml. chlorobenzene, a suspending medium, were mixed and heated for one hour at 100° C. The reaction mixture was cooled, and the chlorobenzene was decanted. The solid product was purified with acetone in usual manner. A quantitative yield of HNS was obtained.

EXAMPLE IX 1.2 g. HNBB, 0.6 g. bromine, 0.6 g. pyridine, and 50 ml. chlorobenzene were mixed and heated for one hour at 100° C. The reaction mixture was cooled and the chlorobenzene was decanted. The product was purified with acetone as usual. A 67% yield of HNS was obtained.

EXAMPLE X 1.2 g. HNBB, 2.0 g. N-bromosuccinimide, 1.2 g. pyridine, and 25 ml. dimethylformamide were mixed and heated two hours at 70° C. The product was recovered from the reaction mixture and purified with acetone as in Example I. The yield of HNS was 85%. A similar reaction was carried out except that no pyridine was employed in the reaction mixture. This gave no HNS product.

EXAMPLE XI 1.2 g. HNBB, 2.0 g. N-bromoacetamide, 1.2 g. pyridine, and 25 ml. dimethylformamide were mixed and heated for two hours at 70° C. The product was separated from the reaction mixture and purified with acetone as in Example I. The yield of HNS was 80%. A similar experiment wherein no pyridine was employed in the reaction mixture produced an 8% yield of HNS.

EXAMPLE XII 1.2 g. HNBB, 1.2 g. N-chlorosuccinimide, 1.2 g. pyridine, and 25 ml. dimethylformamide were mixed and heated for two hours at 70° C. The product was recovered and purified as in Example I. The yield of HNS was 88%. When the experiment was repeated without employing pyridine, a 25% yield of HNS was obtained.

EXAMPLE XIII 2.3 g. HNBB, 1.0 g. bromine, and 25 ml. pyridine were mixed and stirred two hours at 5°-10° C. Recovery and purification of the product as in Example I gave a 26% yield of HNS. This shows that low temperatures are unsatisfactory for practical use.

EXAMPLE XIV 1.2 g. HNBB, 1.2 g. bromine, and 25 ml. dimethylformamide were mixed and heated two hours at 70° C. The starting material was recovered and no HNS was obtained. This shows that without pyridine or another basic material the desired product is not obtained.

EXAMPLE XV 1.2 g. HNBB, 1.2 g. bromine, 1.5 g. of triethylamine, and 25 ml. dimethylformamide were mixed and heated for two hours at 70° C. The product was recovered and purified as in Example I. A 38% yield of HNS was obtained.

EXAMPLE XVI 1.2 g. HNBB, 1.2 g. bromine, 1.0 g. anhydrous sodium carbonate, and 25 ml. dimethylformamide were mixed and heated three-and-a-half hours at 70° C. The product was recovered and purified as in Example I. A 17% yield of HNS was obtained.

EXAMPLE XVII 1.2 g. HNBB, 1.2 g. bromine, 2.0 g. sodium bicarbonate, and 25 ml. dimethylformamide were mixed and heated for three-and-a-half hours at 70° C. The product was recovered and purified as in Example I. A 33% yield of HNS was obtained. No HNS product was obtained using the same reagents at four hours at room temperature.

EXAMPLE XVIII 1.2 g. HNBB, 1.2 g. bromine, 1.0 g. magnesium oxide, and 25 ml. dimethylformamide were mixed and heated for three-and-a-half hours at 70° C. The product was recovered and purified as in Example I. A 42% yield of HNS was obtained. No product was obtained with these reagents when the reaction mixture was kept at room temperature for four hours. This example illustrates that the time and temperature of the reaction play a significant part in the yields.

EXAMPLE XIX 1.2 g. HNBB, 1.2 g. pyridine, and 25 ml. dimethylformamide were mixed and a slow stream of chlorine gas was passed into the solution for ten minutes. The mixture was then heated for two hours at 70° C. The product was recovered and purified as in Example I. The yield of HNS was 21%.

EXAMPLE XX 1.2 g. HNBB, 6 ml. of a 5% aqueous solution of sodium hypochlorite, 0.075 g. sodium hydroxide, and 50 ml. tetrahydrofuran were mixed and stirred for three hours at room temperature. The product was recovered and purified as in Example I. The yield of HNS was 25%. A similar experiment in which no sodium hydroxide was added gave no HNS.

EXAMPLE XXI 1.2 g. of HNBB were dissolved in 15 ml. of hexamethylphosphoramide. 1.0 g. of bromine was added dropwise to the solution at 50° C. and the mixture was then agitated at 50° C. for two hours. The product was recovered and purified as described in Example I. The yield of HNS thus obtained was 0.4 g., corresponding to a yield of 33%.

EXAMPLE XXII

A solution of 1.0 g. of bromine in 15 ml. of dimethylformamide was added dropwise to a mixture of 1.2 g. of HNBB, 1.2 g. of 30% ammonium hydroxide and 15 ml. of dimethylformamide while agitating and maintaining the reaction mixture at 20°–25° C. by external cooling. The miture was then stirred at room temperature for 15 minutes and processed in usual manner to recover a purified HNS product. The yield of HNS thus obtained was 0.3 g., which corresponds to a yield of 25%.

EXAMPLE XXIII

A mixture of 1.2 g. of HNBB, 0.8 g. of iodine and 25 ml. of pyridine was agitated at room temperature for 6 hours. The reaction mixture was worked up in the usual manner to recover and purify the HNS product. The yield of HNS thus obtained was 42% of theory.

I claim:

1. A process for producing 2,2′,4,4′,6,6′-hexanitrostilbene (HNS) which comprises reacting 2,2′,4,4′,6,6′-hexanitrobibenzly (HNBB) with a halogenating agent in the presence of a base in a liquid solvent or suspending agent which is inert to the reaction.

2. The process of claim 1, wherein the reaction is carried out at a temperature within the range of 20° C. and 100° C.

3. The process of claim 1, wherein at least two equivalents of halogenating agent are present per mole of 2,2′,4,4′,6,6′-hexanitrobibenzyl.

4. The process of claim 1 wherein said halogenating agent is selected from the group consisting of bromine, chlorine, N-bromosuccinimide, N-bromacetamide, and N-chlorosuccinimide.

5. The process of claim 1 wherein the base is selected from the group consisting of pyridine, triethylamine, sodium hydroxide, sodium carbonate, sodium bicarbonate and magnesium oxide.

6. The process of claim 5 wherein said solvent of liquid suspending agent is selected from the group consisting of water, pyridine, dimethylformamide, hexamethylphosphoramide, acetonitrile, tetrahydrofuran, 1,4-dioxane, toluene, and chlorobenzene.

7. The process of claim 1 wherein said base is pyridine.

8. The process of claim 1 wherein said halogenating agent is bromine, said base is pyridine, and said solvent is dimethylformamide.

9. The process of claim 1 wherein said halogenating agent is bromine, said base is pyridine, and said solvent is acetonitrile.

10. The process of claim 1 wherein said halogenating agent is bromine, said base is pyridine, and said solvent is tetrahydrofuran.

11. The process of claim 1 wherein said halogenating agent is bromine, said base is pyridine, and said solvent is 1,4-dioxane.

12. The process of claim 1 wherein said halogenating agent is bromine, said base is pyridine, and said liquid suspending agent is toluene.

13. The process of claim 1 wherein said halogenating agent is bromine, said base is pyridine, and said liquid suspending agent is chlorobenzene.

14. The process of claim 1 wherein said halogenating agent is N-bromosuccinimide, said base is pyridine, and said solvent is dimethylformamide.

15. The process of claim 1 wherein said halogenating agent is N-bromoacetamide, said base is pyridine, and said solvent is dimethylformamide.

16. The process of claim 1 wherein said halogenating agent is N-chlorosuccinimide, said base is pyridine, and said solvent is tetrahydrofuran.

* * * * *